United States Patent [19]

Ellner

[11] Patent Number: 4,904,874
[45] Date of Patent: Feb. 27, 1990

[54] APPARATUS FOR IRRADIATING FLUIDS

[75] Inventor: Sidney Ellner, Bedford, N.Y.

[73] Assignee: Ultraviolet Purification Systems, Bedford Hills, N.Y.

[21] Appl. No.: 227,525

[22] Filed: Aug. 2, 1988

[51] Int. Cl.⁴ .............................................. G01N 21/01
[52] U.S. Cl. ................... 250/436; 250/455.1; 250/432 R
[58] Field of Search ............... 250/432 R, 436, 492.1, 250/438, 455.1; 422/24, 26, 28, 44; 378/67; 604/4

[56]  References Cited
U.S. PATENT DOCUMENTS 4,471,225  9/1984  Hillman ............................. 250/436
4,602,162  7/1986  Sperry, III et al. ................ 250/436
4,766,321  8/1988  Lew et al. .......................... 250/436

Primary Examiner—Janice A. Howell
Assistant Examiner—Kiet Nguyen
Attorney, Agent, or Firm—Austin R. Miller

[57]  ABSTRACT

A device for irradiating liquids including a hollow tube capable of transmitting selected wavelengths of light, a drive motor connected to rotate the tube at a desired speed, a support associated with the tube to permit rotation thereof, one or more elongated light producing lamps exteriorly positioned about the tube, the lamps producing light capable of transmission through the cylinder without undue attenuation, a support for the exterior lamps, one or more elongated light producing lamps interiorly positioned about the tube, and a support for the interior lamps.

16 Claims, 2 Drawing Sheets

APPARATUS FOR IRRADIATING FLUIDS

BACKGROUND OF THE INVENTION

The present invention relates to a device fo irradiating fluids, particularly to a device capable of generating ultraviolet light for irradiation and disinfection of fluids such as blood.

FIELD OF THE INVENTION

Over the past several years researchers have attempted to find new and more effective methods of disinfecting and/or treating fluids to kill living organisms such as bacteria and viruses, for example. Of particular interest in light of the recent onset of acquired immune deficiency syndrome (AIDS) is an enhanced desire to find methods insuring safe supplies of blood.

For example, Matthews et al, have recently discovered that the AIDS virus may be destroyed upon treatment with a combination of non-toxic dye and laser light. *The Burlington, Vermont Free Press,* Jan. 13, 1988 edition, page 11a.

Heinrich et al have been successful in sterilizing human plasma with propiolactone and ultraviolet light irradiation to kill viral hepatitis or AIDS. *Dev. Biol. Stand.,* 1987; 67:311-317.

Wallbank et al have employed ultraviolet light in water to inactivate Pseudomonas aeruginosa and poliovirus. *Lab. Anim.,* 1985 Oct.; 19(4):273-4.

Stephan et al have successfully sterilized chimpanzee serum by treatment with propiolactone and ultraviolet irradiation to kill infectious hepatitis B virus. *Vox. Sang.* 1981 Sep.; 41(3):134-8

In view of these rapid advancements in treating various fluids with irradiating light, it has now become necessary to provide a convenient and effective apparatus to perform these tasks.

DESCRIPTION OF THE PRIOR ART

Applicant is aware of the following U.S. Patents relating to apparatus for treatment of fluids with ultraviolet light: 2,047,470; 3,557,783; 4,428,744 and 4,576,143. Of these, 4,428,744 and 4,576,143 appear to be the most pertinent.

'477 discloses a system for externally treating blood. A radiation source irradiates blood flowing through a radiation chamber wherein multiple ultraviolet lamps irradiate a coiled tube as blood flows therethrough. The tube is preferably flattened with its interior thickness ranging from about 0.05-10 mm.

'143 discloses a method and apparatus for extracorporeal irradiation of blood. The apparatus consists of X-rays emitting from a lamp and irradiating blood flowing through a coiled tube. The tube is preferably constructed of a polyvinyl chloride which permits passage of x-ray through the tube walls to the flowing blood.

Applicant is further aware of an apparatus described by Wallbank et al wherein water passes through a teflon pipe and is irradiated with ultraviolet light. *Lab. Anim.* 1985 Oct; 19(4):273-4.

OBJECTS OF THE INVENTION

It is an object of the present invention to provide a device capable of irradiating fluids to kill selected living organisms contained within the fluid.

It is another object of the present invention to provide a device for irradiating fluids capable of operating in a continuous mode to efficiently irradiate and disinfect large quantities of fluid.

It is an important object of the present invention to provide a device capable of irradiating fluids which is easy to operate, is safe to the user and requires little or no maintenance.

It is still another object of the present invention to provide a device for irradiating opaque fluids to kill selected living organisms within the fluid.

It is a further object of the present invention to provide a device capable of irradiating human blood to kill deadly viruses such as AIDS, hepatitis and the like.

Other objects and advantages of the present invention will become apparent to those skilled in the art from the drawings, the detailed description of preferred embodiments and the appended claims.

SUMMARY OF THE INVENTION

The present invention provides a device for subjecting fluids to irradiating light. The device consists of a hollow cylinder capable of transmitting germicidal wavelengths of light and is connected to a drive motor for rotation at a desired speed. The cylinder is supported by pairs of rollers positioned underneath the cylinder and at each end. The cylinder can be rotated directly by the motor or by way of the rollers connected to the motor. A multiplicity of ultraviolet light producing lamps surrounds the exterior of the rotatable cylinder. The lamps are preferably surrounded by a cylinder having a reflective surface to direct light inwardly toward the cylinder.

A further set of ultraviolet light producing lamps is positioned within the cylinder and are supported by a core member located interiorly of the lamps. The core member preferably has a reflective surface to direct ultraviolet light outwardly toward the cylinder.

DETAILED DESCRIPTION OF THE INVENTION

Figure 1:
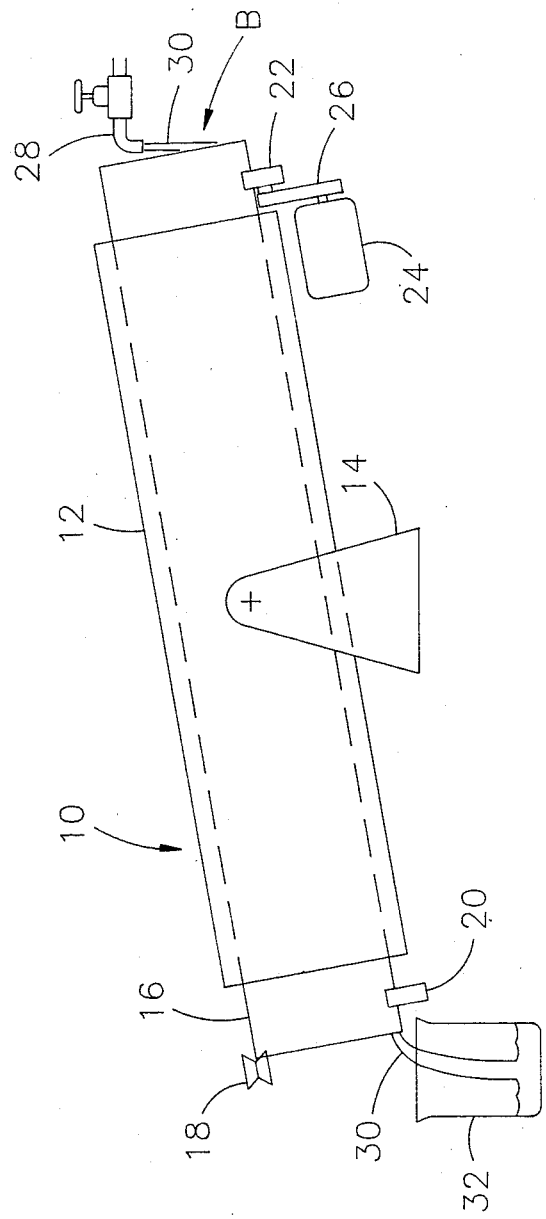
FIG. 1 shows a schematic side view of apparatus in accordance with aspects of the invention.

It will be appreciated that the following description is intended to refer to the specific embodiment of the invention selected for illustration in the drawings and is not intended to define or to limit the invention, other than in the appended claims.

Turning now to the specific form of the invention illustrated in the drawings, and referring particularly to FIG. 1, the number 10 designates a fluid irradiation device in accordance with aspects of the invention. Device 10 has an outer cylinder 12 connected to support 14. Inner cylinder 16 is disposed within outer cylinder 12 and is maintained laterally within outer cylinder 12 by rolling stop member 18. Similarly, inner cylinder 16 is supported within outer cylinder 12 by support rollers 20 and 22. Motor 24 connects to belt 26 which connects to support roller 22.

Fluid supply pipe 28 supplies fluid 30 into one end of inner cylinder 16 which exits into fluid container 32 at the opposite end of inner cylinder 16.

Figures 2, 3:
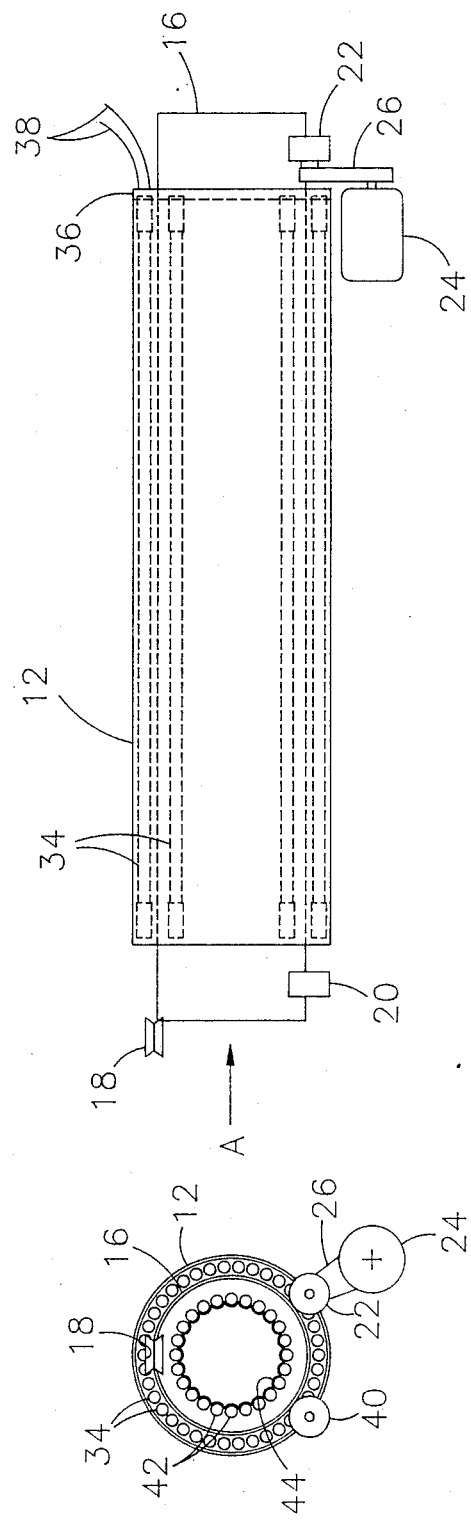
FIG. 2 shows a schematic side view of the apparatus of the invention, outlining selected internal portions of the apparatus.
FIG. 3 shows a schematic end view of the apparatus shown in FIG. 2, taken from the direction of arrow A.

Referring now to FIG. 2, inner cylinder 16 resides primarily within outer cylinder 12 and is maintained in its lateral position by rolling stop member 18. Support rollers 20 and 22 support inner cylinder 16. Motor 24 connects to belt 26 which connects to support roller 22. Lamps 34 reside interiorly of outer cylinder 12 and connect on one end to lamp connector 36 which connects to power supply wires 38.

FIG. 3 shows motor 24 connected to belt 26 which connects to roller 22. Roller 40 supports the other side of outer cylinder 12 in concert with roller 22. Rolling stop member 18 restricts lateral movement of inner cylinder 16 with respect to outer cylinder 12. Exterior lamps 34 are disposed between outer cylinder 12 and inner cylinder 16. Interior lamps 42 are located between inner cylinder 16 and light reflector 44.

Referring now to the drawings generally, the operation of device 10 will now be described.

Outer cylinder 12 connects to support 14 and remains substantially stationary during irradiation of fluids. Support 14 is preferably designed to permit tilting of outer cylinder 12 to either increase or decrease passage of fluids 30 through device 10 depending upon the degree of irradiation desired. Prior to introduction of the fluid to be disinfected, motor 24 is activated, which rotates belt 26. Belt 26 connects to support roller 22 and rotates it at the desired speed.

Inner cylinder 16 is free to rotate because it is supported by pair of rollers 20 and 22. Fluid 30 is directed by way of fluid supply pipe 28 into the raised end indicated by arrow B. Inner cylinder 16 rotates at a desired speed sufficiently high to cause fluid 30 to contact the inner surface of inner cylinder 16 by centrifugal force. Rotation speed of inner cylinder 16, tilt of cylinders 12 and 16 and rate of input of fluid 30 are controlled to preferably maintain fluid thickness at about 1-3 molecular thicknesses. This insures proper exposure to the irradiating light.

Inner cylinder 16 is preferably constructed of quartz to permit passage of ultraviolet light rays without undue attenuation. This is especially important in view of the relative capacity of fluids such as blood. Opacity of the fluid has heretofore substantially reduced the ability to completely and uniformly expose the fluid to the necessary quantity of irradiation to achieve the desired killing of organisms within the fluid. A cylinder constructed of quartz permits transmittal of light wavelengths capable of killing desired organisms without undue attenuation.

The time of exposure of fluid 30 within device 10 may be closely controlled by a combination of the speed of rotation of inner cylinder 16, the rate of supply of fluid 30 within inner cylinder 16 and the degree of tilt of the respective cylinders 12 and 16 out of horizontal. The device is specifically designed to achieve high speeds of rotation to drive the fluid tightly against the inner surface of inner cylinder 16. Rotation speed may be altered so long as it maintains its centrifuge effect on the fluid. Degree of tilt and rate of supply are manipulated in conjunction with rotation speed to reduce the thickness of fluid 30 lying against the inner surface of inner cylinder 16 to a magnitude of order of molecular thicknesses. Disinfection capabilities are increased when the opacity inherent in many fluids 30 is reduced by lowering fluid thickness at points of light exposure to permit penetration of the entire fluid layer. The construction of the instant device provides this for the first time.

Power to lamps 34 and 42 is supplied by wires 38 and lamp connector 36. Lamps 34 and 42 are ultraviolet light producing lamps. Exterior lamps 34 direct ultraviolet light inwardly through inner cylinder 16 to irradiate fluid as it travels longitudinally along the length of the cylinder. Similarly, interior lamps 42 direct ultraviolet light outwardly toward fluid 30 residing on the inner surface of inner cylinder 16. Light reflector 44 serves as a support for lamps 42 and preferably provides reflection of light rays radially outwardly. Outer cylinder 12 is preferably fitted with a reflective interior surface to assist in the radially inward direction of ultraviolet light rays. Rolling stop member 18 prevents inner cylinder 16 from sliding longitudinally with respect to inner cylinder 12 horizontal during rotation.

Although the drawings indicate a single electric motor 24 driven by belt 26, it is within the scope of the invention that other drive devices and connection methods may be used. Other suitable drive means could include chain drive or gears or the like. It is further within the scope of the invention to drive transparent cylinder 16 without connection to roller 22.

Similarly, the lamp connections shown in FIG. 2 are preferred embodiments. Other means of supplying power to lamps 36 and 42 are possible as well as different types of lamps 36 and 42, such as lamps having electrical connections on both ends.

It is further within the scope of the invention to include a support means other than that shown by support 14. For example, it is possible to supply separate support means on both ends of outer cylinder 12 which may be raised and lowered in combination or individually to achieve tilting action of the respective cylinders 12 and 16.

It is still further within the scope of the invention to include one or more light intensity measuring devices among lamps 34 and 42. Such measuring devices can be in addition to lamps 34 and 42 or may be substituted for a lamp 34 or 42.

Although this invention has been described in connection with specific forms thereof, it will be appreciated that a wide array of equivalents may be substituted for the specific elements shown and described herein without departing from the spirit and scope of this invention as described in the appended claims.

We claim:

1. Apparatus for irradiating fluids comprising:
   a hollow tube capable of transmitting selected wavelengths of light;
   drive means connected to rotate said tube at a desired speed;
   support means associated with said tube to permit rotation thereof;
   one or more elongated light producing lamps exteriorly positioned about said tube, said lamps producing light capable of transmission through said cylinder without undue attenuation;
   means to support said exterior lamps;
   one or more elongated light producing lamps interiorly positioned about said tube; and
   means to support said interior lamps.

2. Apparatus defined in claim 1, wherein said tube comprises quartz.

3. Apparatus defined in claim 1, wherein said interior and exterior lamps produce ultraviolet light.

4. Apparatus defined in claim 1, wherein said drive means comprises an electric motor.

5. Apparatus defined in claim 1, wherein said support means comprises pairs of spaced apart rollers positioned beneath and contacting each end of said tube.

6. Apparatus defined in claim 1, wherein said means to support said exterior lamps comprises a cylindrically shaped cover positioned exteriorly of said exterior lamps and is connected thereto.

7. Apparatus defined in claim 6, wherein said cover has a reflective inner surface to reflect light inwardly toward said tube.

8. Apparatus defined in claim 1, wherein said meas to support said interior lamps comprises a cylindrically shaped core member positioned interiorly of said interior lamps and is connected thereto.

9. Apparatus defined in claim 8, wherein said core member has a reflective outer surface to reflect light outwardly toward said tube.

10. Apparatus as defined in claim 1 further comprising a light intensity measuring device positioned exteriorly of said tube.

11. Apparatus defined in claim 1 further comprising a light intensity measuring device positioned interiorly of said tube.

12. Apparatus defined in claim 1 further comprising means to tilt said tube out of horizontal to control the flow of fluid therethrough.

13. Apparatus defined in claim 1 further comprising means to restrict horizontal movement of said tube.

14. Apparatus defined in claim 1, wherein said lamps have electrical connections at one end only.

15. Apparatus defined in claim 5, wherein said drive means rotates one or more of said rollers, thereby inducing rotation of said tube.

16. Apparatus defined in claim 1, wherein said tube is cylindrically shaped.

* * * * *